United States Patent
Orts et al.

(10) Patent No.: US 10,105,536 B2
(45) Date of Patent: Oct. 23, 2018

(54) FIXATION SLEEVE EQUIPPED LEADLESS PULSE GENERATOR

(71) Applicant: PACESETTER, INC., Sylmar, CA (US)

(72) Inventors: Sondra Orts, Sunnyvale, CA (US); Carl Lance Boling, San Jose, CA (US); Matthew G. Fishler, Santa Cruz, CA (US); Benjamin F. James, IV, Canyon Country, CA (US); Xiangqun Chen, Santa Clarita, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/872,616

(22) Filed: Jan. 16, 2018

(65) Prior Publication Data

US 2018/0133465 A1 May 17, 2018

Related U.S. Application Data

(62) Division of application No. 14/884,619, filed on Oct. 15, 2015, now Pat. No. 9,907,953.

(51) Int. Cl.
| | |
|---|---|
| *A61N 1/00* | (2006.01) |
| *A61N 1/05* | (2006.01) |
| *A61N 1/362* | (2006.01) |
| *A61N 1/375* | (2006.01) |
| A61B 90/00 | (2016.01) |

(52) U.S. Cl.
CPC .......... *A61N 1/0573* (2013.01); *A61N 1/362* (2013.01); *A61N 1/3756* (2013.01); *A61B 2090/3966* (2016.02)

(58) Field of Classification Search
USPC ........................................... 607/127
See application file for complete search history.

(56) References Cited

U.S. PATENT DOCUMENTS

| | | | |
|---|---|---|---|
| 7,801,624 | B1 | 9/2010 | Flannery et al. |
| 7,937,148 | B2 | 5/2011 | Jacobson |
| 7,945,333 | B2 | 5/2011 | Jacobson |
| 8,010,209 | B2 | 8/2011 | Jacobson |
| 8,352,025 | B2 | 1/2013 | Jacobson |

(Continued)

FOREIGN PATENT DOCUMENTS

| | | |
|---|---|---|
| WO | 2007047681 A2 | 4/2007 |
| WO | 2007047681 A3 | 9/2008 |
| WO | 2007047681 | 11/2008 |

*Primary Examiner* — Nicole F Johnson (57) ABSTRACT

A leadless pulse generator is disclosed herein. The leadless pulse generator has a body, a helical anchor, an electrode, and a sleeve. The body includes a distal end and a proximal end opposite the distal end. The helical anchor distally extends from the distal end. The electrode is at the distal end. The sleeve distally extends from the distal end and has a proximal face and a distal face opposite the proximal face. The proximal face is adjacent the body. The sleeve coaxially extends about the helical anchor and further has a biased state wherein the distal face is near a distal tip of the helical anchor. The sleeve is configured to compress such that the distal face displaces proximally towards the proximal face upon the distal face being forced against the cardiac tissue in the course of the helical anchor screwing into the cardiac tissue.

5 Claims, 8 Drawing Sheets

(56) References Cited

U.S. PATENT DOCUMENTS

| | | |
|---|---|---|
| 8,457,742 B2 | 6/2013 | Jacobson |
| 9,216,285 B1 | 12/2015 | Boling |
| 2007/0050003 A1 | 3/2007 | Zarembo et al. |
| 2007/0088396 A1 | 4/2007 | Jacobson |
| 2007/0088397 A1 | 4/2007 | Jacobson |
| 2010/0222855 A1 | 9/2010 | Hill et al. |
| 2010/0222860 A1 | 9/2010 | Casella et al. |
| 2016/0096001 A1* | 4/2016 | Eidenschink ....... A61M 25/008 606/129 |

* cited by examiner

FIXATION SLEEVE EQUIPPED LEADLESS PULSE GENERATOR

CROSS REFERENCE TO RELATED APPLICATIONS

This is a division of U.S. patent application Ser. No. 14/884,619, filed Oct. 15, 2015.

FIELD OF THE INVENTION

Aspects of the present invention relate to medical apparatus and methods. More specifically, the present disclosure relates to leadless pulse generators equipped with fixation sleeves. The present disclosure also relates to methods of manufacturing and using such leadless pulse generators.

BACKGROUND OF THE INVENTION

Leadless pulse generators have a helical anchor at a distal end of the leadless pulse generator. The helical anchor is used to secure the leadless pulse generator to cardiac tissue in such a manner that an electrode of the leadless pulse generator is maintained in appropriate tissue contact for cardiac pacing and sensing.

Since the helical anchor is fixed relative to the rest of the leadless pulse generator, the leadless pulse generator is rotated as a whole relative to the cardiac tissue to cause the helical anchor to screw into the cardiac tissue and thereby fix the leadless pulse generator to the cardiac tissue. Implanters make use of a chevron or other shaped radiopaque marker within the body of the device for visual feedback under fluoroscopy when rotating the leadless pulse generator to screw the helical anchor into the cardiac tissue.

A prescribed number of turns (e.g. 1¼ turns) of the leadless pulse generator is recommended for desirable helical anchor fixation in the cardiac tissue. However, verifying that the prescribed number of turns has actually resulted in actual turns of the helical anchor screwing into the cardiac tissue can be a challenge. This challenge results from the fact that the leadless pulse generator may be rotated for the prescribed number of turns without the helical anchor fully engaging the cardiac tissue for the entirety of the prescribed number of turns, and the radiopaque marker viewed via fluoroscopy only conveys to the implanter that rotation of the leadless pulse generator is occurring, not that the helical anchor is properly screwing into cardiac tissue.

Consequently, there is a need in the art for an improved leadless pulse generator configuration and related methods of manufacture and use.

BRIEF SUMMARY OF THE INVENTION

A leadless pulse generator for administering therapy to cardiac tissue is disclosed herein. In one embodiment, the leadless pulse generator includes a body, a helical anchor, an electrode, and a sleeve. The body includes a distal end and a proximal end opposite the distal end. The helical anchor distally extends from the distal end. The electrode is at the distal end. The sleeve distally extends from the distal end and includes a proximal face and a distal face opposite the proximal face. The proximal face is adjacent the body. The sleeve coaxially extends about the helical anchor and further includes a biased state wherein the distal face is near a distal tip of the helical anchor. The sleeve is configured to compress such that the distal face displaces proximally towards the proximal face upon the distal face being forced against the cardiac tissue in the course of the helical anchor screwing into the cardiac tissue. The sleeve may be radiopaque or include a radiopaque portion or component.

In one embodiment, the leadless pulse generator further includes an anchor mount operably coupled to the distal end and supporting the helical anchor. A portion of the sleeve is sandwiched between the anchor mount and the distal end. The portion of the sleeve may be a radially inward extending annular ring. The electrode may be exposed at a center of the anchor mount, and the anchor mount may be threadably, interference or press fit, swaged, welded, or otherwise operably coupled to the distal end.

In one embodiment, the sleeve includes a proximal section extending distally from the proximal face and a distal section extending proximally from the distal face. The sleeve is configured such that, in the course of the helical anchor screwing into the cardiac tissue and the distal face being forced against the cardiac tissue, the distal section folds proximally and the distal face increases in diameter.

In one embodiment, when the sleeve is in the biased state, the distal section includes a conical outer shape and the proximal section includes a cylindrical outer shape. The conical outer shape distally increases in diameter, The distal face may change from facing distally to facing radially outward when the distal face displaces proximally towards the proximal face.

In one embodiment, the distal section includes a series of longitudinally extending gaps and longitudinally extending members. The members distally terminate as part of the distal face. The gaps and members are arranged in a uniformly spaced alternating fashion about a circumference of the distal section. The members may be wider than the gaps, or the gaps may be wider than the members. The members may change from projecting distally to projecting radially outward when the distal face displaces proximally towards the proximal face.

In one embodiment, the sleeve includes a proximal cylindrical section extending distally from the proximal face and a distal bellows section extending proximally from the distal face. The distal bellows section includes first and second radially outward projecting circumferentially extending ridges and a radially inward projecting circumferentially extending valley located between the first and second ridges. The sleeve is configured such that, in the course of the helical anchor screwing into the cardiac tissue and the distal face being forced against the cardiac tissue, the first ridge moves proximally towards the second ridge and the valley decreases in dimension distal-proximal.

A method of manufacturing a leadless pulse generator is also disclosed herein. In one embodiment, the method includes: positioning a distal electrode of the leadless pulse generator within a hollow interior of a compressible fixation sleeve including at least a radiopaque portion; and coupling the compressible fixation sleeve to the housing of the leadless pulse generator by coupling an anchor mount to the housing such that a portion of the compressible fixation sleeve is sandwiched between the anchor mount and a portion of the housing.

The sandwiched portion of the compressible fixation sleeve may be in the form of an inner annular ring. The housing may include a distal protrusion that boarders the distal electrode and is also positioned in the hollow interior. The distal protrusion may mechanically couple with the anchor mount when the anchor mount is coupled to the housing. For example, the distal protrusion and the anchor mount may threadably engage with each other in the course of being mechanically coupled with each other.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The description will be more fully understood with reference to the following figures, which are presented as various embodiments of the disclosure and should not be construed as a complete recitation of the scope of the disclosure, wherein.

DETAILED DESCRIPTION

The present disclosure is directed to a leadless pulse generator 120 including a compressible fixation sleeve 130 supported on a distal end of the leadless pulse generator 120, the sleeve 130 coaxially extending about a helical anchor 66 distally projecting from the distal end of the leadless pulse generator. At least a portion of the sleeve 130 is radiopaque. The sleeve 130 is configured to bias distally such that the wall structure of the sleeve circumferentially extends about the anchor 66 to protect the anchor from engagement with cardiovascular tissue in the course of tracking to an implantation site in a patient's heart. The sleeve 130 is configured to proximally compress as a distal face 134 of the sleeve 130 abuts against cardiac tissue into which the anchor 66 is being screwed, the distal displacement of the distal face 134 relative to the distal tip of the anchor 66 and/or the proximal face 132 of the sleeve 130 providing information to an implanter via fluoroscopy as to whether or not the anchor 66 is actually screwing into the cardiac tissue of the implant site.

In addition to providing an indication of anchoring of the anchor 66 into cardiac tissue and protecting against inadvertent tissue damage from the anchor while implanting, relocating or retrieving the leadless pulse generator, the sleeve 130 also provides other benefits. Examples of such other benefits include providing resistance against over-rotation of the leadless pulse generator during implant, and a wider contact surface to reduce contact pressure and mitigate tissue damage. Also, the sleeve 130 can form a seal against the endocardium to reduce the possibility of effusion through a potential microperforation created by the anchor 66 extending through the thin myocardium. Finally, the compressible sleeve 130 can act to prevent anti-rotation of an implanted leadless pulse generator 120.

Before beginning a discussion regarding the details of the fixation sleeves 130 disclosed herein, a general discussion will first be given regarding electrotherapy systems employing leadless pulse generators 120.

a. Electrotherapy System Employing Leadless Pulse Generator

Figure 1:
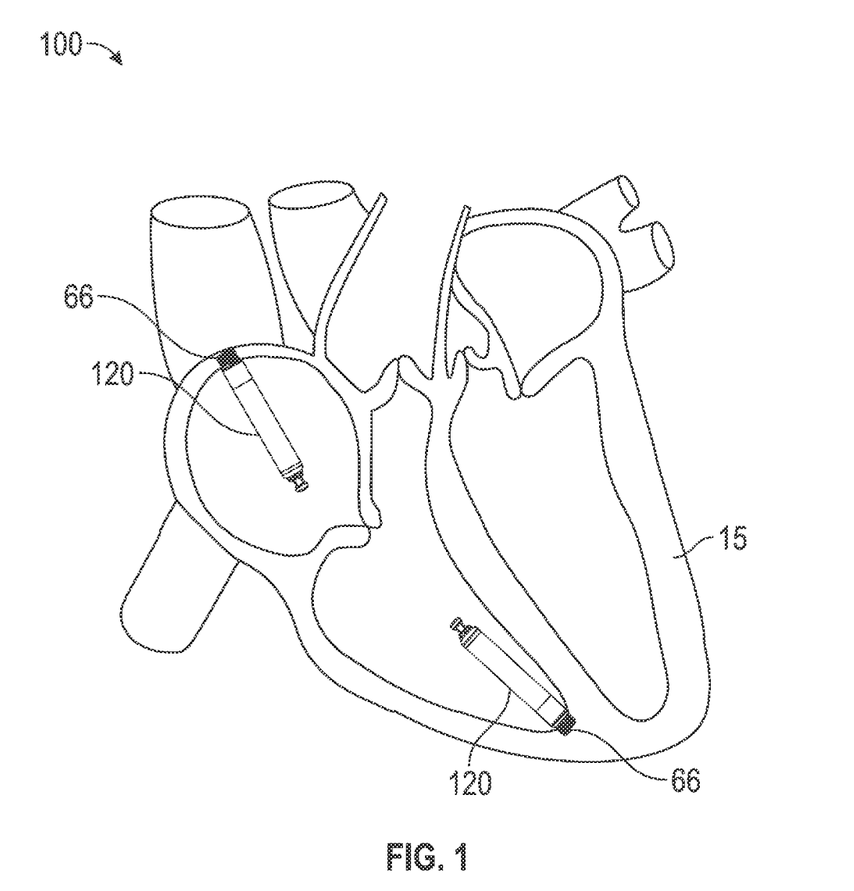
FIG. 1 is a diagrammatic depiction of a leadless electrotherapy system electrically coupled to a patient heart as viewed from an anterior side of the patient heart.

FIG. 1 is a diagrammatic depiction of a leadless electrotherapy system 100 electrically coupled to a patient heart 15 as viewed from an anterior side of the patient heart. The leadless electrotherapy system 100 employs one or more leadless pulse generators 120 (e.g., leadless pacemaker, leadless implantable cardioverter defibrillator (leadless-ICD), or etc.). As discussed in greater detail below, each leadless pulse generator 120 is substantially enclosed in a hermetic housing suitable for placement on or attachment to the inside or outside of a cardiac chamber. The leadless pulse generator can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner. In alternative embodiments, the housing may contain circuits for receiving and/or transmitting information via other communication means including, for example, Bluetooth, etc.

In some embodiments, a leadless pulse generator 120 can be adapted for implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker. for pacing the cardiac chamber upon receiving a triggering signal from at least one other device within the body.

Self-contained or leadless pulse generators are typically fixed to an intracardiac implant site by an actively engaging mechanism such as a screw or helical member that screws into the myocardium. Examples of such leadless pulse generators are described in the following publications, the disclosures of which are incorporated by reference in their respective entireties herein: (1) U.S. Pat. No. 8,457,742; (2) U.S. Published Application 2007/0088396A1; (3) U.S. Published Application 2007/0088397A1; (4) U.S. Pat. No. 8,352,025; (5) U.S. Pat. No. 7,937,148; (6) U.S. Pat. No. 7,945,333; (7) U.S. Pat. No. 8,010.209; and (8) Int'l Publication No. WO07047681A2.

Figure 2A:
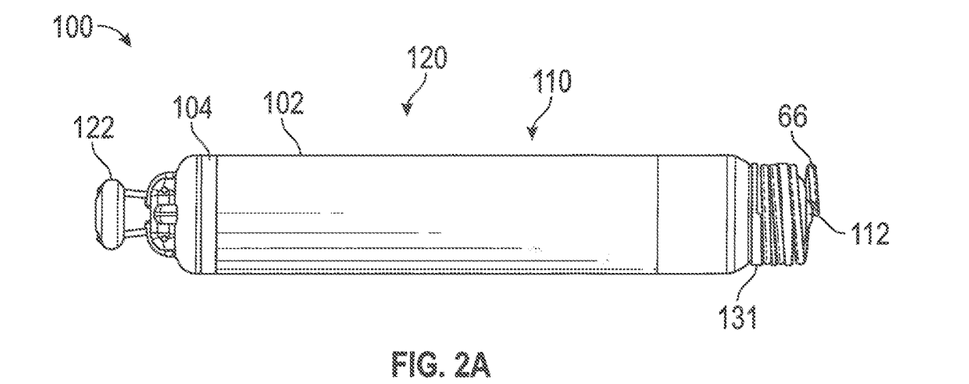
FIG. 2A is a side view of a leadless pulse generator that is generally representative of any of the leadless pulse generators depicted in FIG. 1.
Figure 2B:
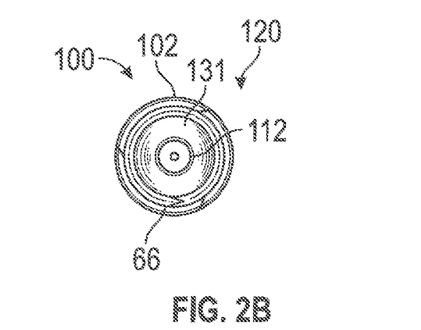
FIG. 2B is a distal end view of the leadless pulse generator of FIG. 2A.

To begin a more detailed discussion of the features of a leadless pulse generator, reference is made to FIGS. 2A and 2B, which are, respectively, a side view and a distal end view of a leadless pulse generator 120 as manufactured by St. Jude Medical, Inc. as its NANOSTIM™ leadless pacemaker. As can be understood from FIGS. 2A and 2B, the leadless pulse generator 120 can include a hermetic housing 102 with a proximal electrode 104 at a proximal end of the leadless pulse generator and a distal electrode 112 at a distal end of the leadless pulse generator.

As shown in FIGS. 2A and 2B, the distal electrode 112 can be in the form of a distal tip electrode 112. In other embodiments, the distal electrode 112 can be in the form of a distal ring electrode. In some embodiments, the distal electrode 112 can be integrated within a helical fixation anchor 66 solely or combined with a distal tip or ring electrode. The distal electrode 112 and the helical anchor 66 are supported on the housing 102.

The proximal electrode 104 can be disposed on the housing 102 in the form of a ring electrode 104. The helical fixation anchor 66 can be in the form of a helically wound wire or other structure capable of screwing into tissue for attaching the housing to tissue, such as heart tissue. The helical fixation anchor 66 can be electrically inert in that it does not act as an electrode. Alternatively, the anchor 66 can be electrically active wherein the anchor 66 is yet another electrode or acts as an extension of, or part of, the distal electrode 112.

The housing can also include an electronics compartment 110 within the housing that contains the electronic components necessary for operation of the pulse generator. The hermetic housing 102 can be adapted to be implanted on or in a human heart, and can be cylindrically shaped, rectangular, spherical, or any other appropriate shape, for example.

The housing 102 can include a conductive, biocompatible, inert, and anodically safe material such as titanium, 316L stainless steel, or other similar materials. The housing can further include an insulator disposed on the conductive material to separate electrodes 104 and 112. The insulator can be an insulative coating on a portion of the housing between the electrodes, and can include materials such as silicone, polyurethane, parylene, or another biocompatible and biostable electrical insulator commonly used for implantable medical devices. In one embodiment, a single insulator is disposed along the portion of the housing between electrodes 104 and 112. In some embodiments, the housing itself can include an insulator instead of a conductor, such as an alumina ceramic or other similar materials, and the electrodes can be disposed upon the housing.

In one embodiment, the leadless pulse generator 120 can include a header assembly to isolate electrode 104 from electrode 112. The header assembly can be made from tecothane or another biocompatible plastic, and can contain a ceramic to metal feedthrough, a glass to metal feedthrough, or other appropriate feedthrough insulator as known in the art.

The electrodes 104 and 112 can include pace/sense electrodes, or return electrodes. A low-polarization coating can be applied to the electrodes, such as platinum, platinum-iridium, iridium, iridium-oxide, titanium-nitride, carbon, or other materials commonly used to reduce polarization effects, for example. In FIG. 2A, electrode 112 can be a pace/sense electrode and electrode 104 can be a return electrode. The electrode 104 can be a portion of the conductive housing 102 that does not include an insulator.

As can be understood from FIG. 2A, the leadless pulse generator 120 can also include a delivery/recovery structure 122 at the extreme proximal end of the leadless pulse generator with which a delivery device (e.g., delivery catheter) can interface in the implantation or removal of the leadless pulse generator.

As illustrated in FIGS. 2A and 2B, the leadless pulse generator 120 can include an anchor mount 131 that is threadably, interference or press fit, swaged, welded, or otherwise secured to the distal end of the housing 102 and extends about the distal electrode 112, which distally protrudes from a distal end of the anchor mount 131. The helical anchor 112 is affixed via mechanical means such as welding, press-fit, or other means to the anchor mount 131 such that the anchor mount being threadably or otherwise secured to the housing 102 results in the anchor 112 being secured to the housing.

Figure 2C:
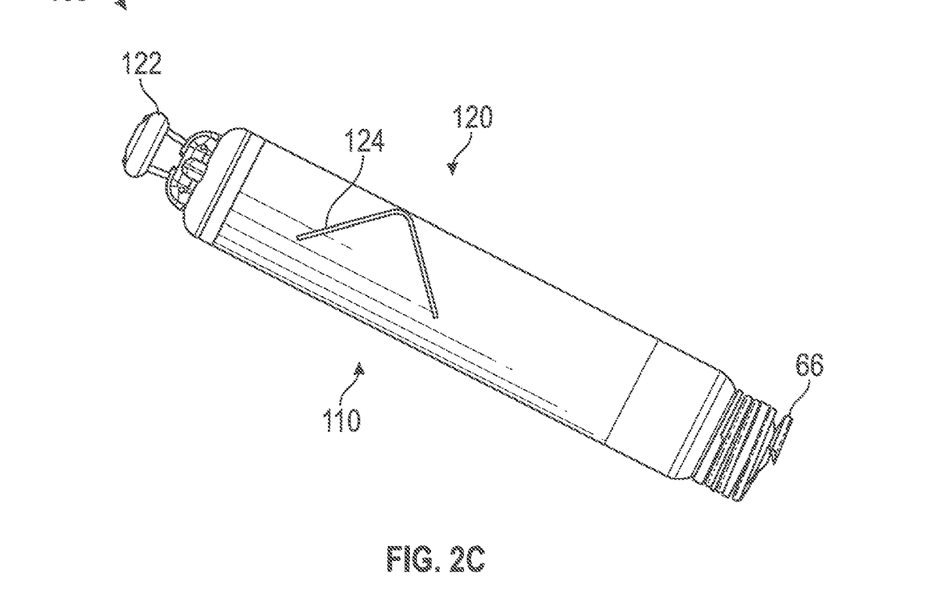
FIG. 2C is a side view of the leadless pulse generator as it appears via fluoroscopy and depicting a chevron-shaped rotation direction indicator that is part of the leadless pulse generator.

As can be understood from FIG. 2C, which is a side view of the leadless pulse generator as it appears via fluoroscopy, the leadless pulse generator 120 can include a chevron-shaped rotation direction indicator 124 supported on, or within, the leadless pulse generator. The chevron 124 is radiopaque, and implanters can use the chevron shaped radiopaque marker 124 for visual feedback under fluoroscopy when rotating the leadless pulse generator to screw the helical anchor into the cardiac tissue.

Figure 3:
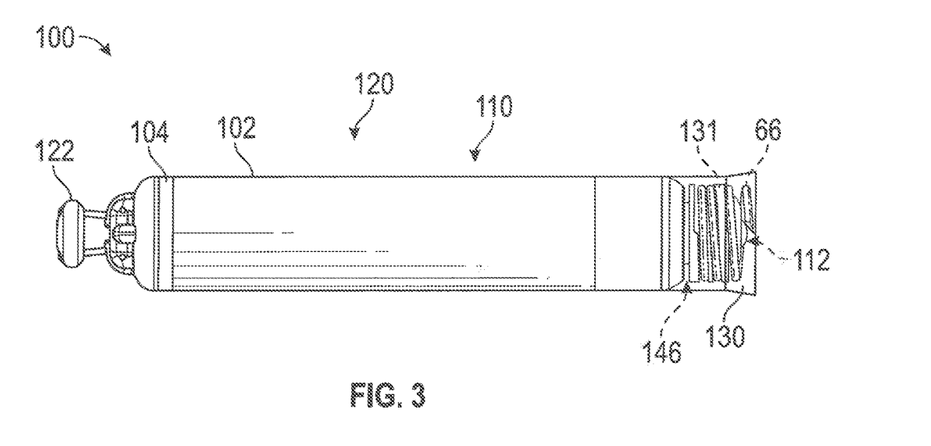
FIG. 3 is a side view of the leadless pulse generator of FIGS. 2-A-2C, except illustrating the leadless pulse generator as being equipped with a compressible radiopaque (or at least partially radiopaque) fixation sleeve.

Several techniques and structures can be used for attaching the housing 102 to the interior or exterior wall of the heart as depicted in FIG. 1. The leadless pulse generator can be delivered endocardially or epicardially through a guiding catheter. A torqueable catheter can be used to rotate the housing and force the helical fixation anchor 66 into heart tissue, thus affixing the fixation anchor (and also the distal electrode in FIG. 2A) into contact with stimulatable tissue, as illustrated in FIG. 1. Electrode 104 can serve as an indifferent electrode for sensing and pacing. The fixation anchor may be coated partially or in full for electrical insulation, and a steroid-eluting matrix may be included on or near the device to minimize fibrotic reaction, as is known in conventional pacing electrode-leads. The helical fixation anchor 66 may be fixed or extendable/retractable relative to the distal end of the leadless pulse generator 120.

b. Compressible Radiopaque Fixation Sleeve Distally Extending from Leadless Pulse Generator Housing and Circumferentially Extending About Helical Fixation Anchor FIG. 3 is a side view of the leadless pulse generator 120 of FIGS. 2-A-2C, except illustrating the leadless pulse generator as being equipped with a compressible radiopaque (or at least partially radiopaque) fixation sleeve 130 that extends distally from the housing 102 or another portion of the leadless pulse generator 120 and circumferentially extends about the helical fixation anchor 66 of the leadless pulse generator. The sleeve 130 extends to the distal end of the helical anchor 66. During anchor fixation to the endocardium at implant, the fixation sleeve is intended to compress axially from its biased distally projecting state and optionally expand radially while the helical anchor 66 within the fixation sleeve 130 screws into cardiac tissue.

The fixation sleeve 130 is advantageous for a number of reasons. First, the sleeve 130 protects cardiac tissue and traversed vasculature from potential trauma as may be caused by interaction with the helical anchor 66 during implant, explant and re-positioning.

Second, the fixation sleeve 130 can act as an indicator of tissue engagement. Once the leadless pulse generator 120 begins to rotate and the anchor tip engages tissue, the fixation sleeve 130 will be compressed as the anchor/tissue engagement increases. Implanters will be able to visually compare the distal edge of the radiopaque fixation sleeve 130 with the helical anchor position and/or the distal end of the pacing electrode 112. Once the radiopaque fixation sleeve 130 is compressed sufficiently such that the distal edge of the sleeve is aligned with the pacing electrode 112, the implanter can be confident that the fixation is fully engaged and the electrode 112 is in contact with the tissue.

Third and as discussed in detail below, optional antirotation features of the fixation sleeve 130 can prevent anchor dislodgement once the fixation sleeve is compressed. Since fixation sleeve compression also results in radial expansion, tine features at the end of the expanded fixation sleeve 130 can help resist anti-rotation of the leadless pulse generator 120 once helical anchor fixation is achieved.

Fourth, if the helical anchor 66 inadvertently pierces transmurally through a very thin region of the atrial or ventricular wall, the fixation sleeve 130 may act as an effective barrier to the effusion of blood out of the heart and into the pericardial space through that micro-perforation.

Finally, the fixation sleeve 130 can be used as a guard against over-rotation and tissue damage. Sleeve bonding at the base of the fixation sleeve 130, as well as radial expansion of the fixation sleeve, can act as a stop against over-rotation of the leadless pulse generator 120 and its potential resulting tissue damage. As the fixation sleeve 130 compresses, the surface area against the tissue will grow, thereby decreasing the contact pressure through increased contact surface area. Additional surface area contact will reduce the likelihood of tissue damage as compared to leadless pulse generators not equipped with the fixation sleeve.

Figures 4A, 4B:
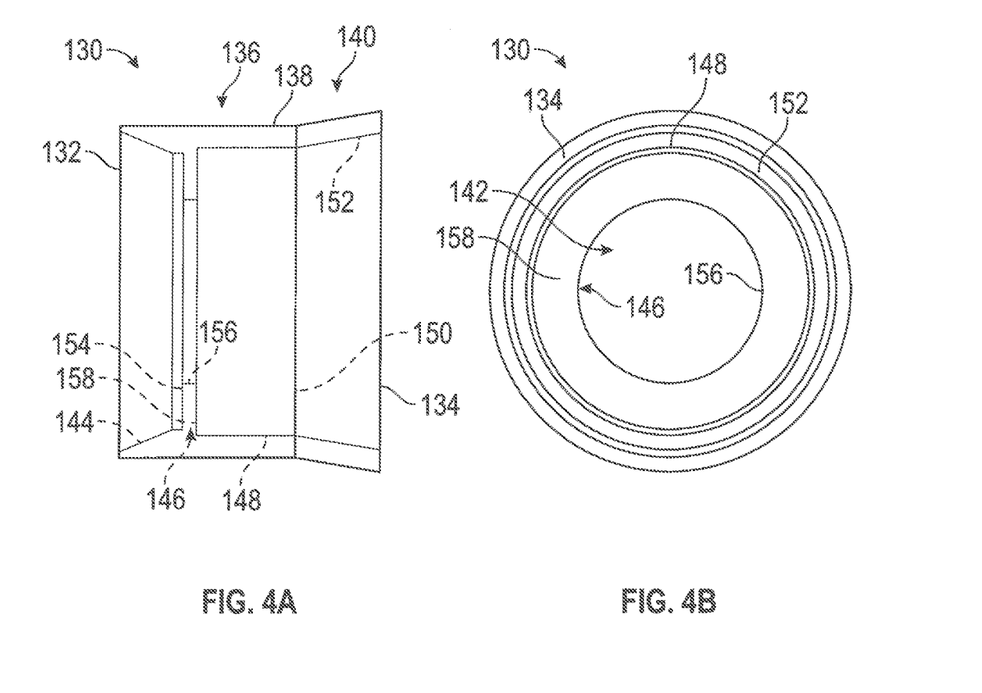
FIG. 4A is an enlarged side view of the compressible fixation sleeve employed with the leadless pulse generator of FIG. 3.
FIG. 4B is an end view of the compressible fixation sleeve of FIG. 4A.

As can be understood from FIGS. 4A and 4B, which are, respectively, enlarged side and end views of the fixation sleeve 130 employed with the leadless pulse generator 120 of FIG. 3, the sleeve 130 includes a proximal face 132 and a distal face 134 opposite the proximal face. An exterior proximal cylindrical section 136 extends distally from the proximal face to an exterior transition 138 to an exterior distal conical section 140 that extends distally from the exterior transition 138 to the distal face 134, which has a diameter that is greater than a diameter of the proximal face 132. Thus, the exterior distal conical section 140 provides the sleeve 130 with a distally flared exterior as compared to the cylindrical exterior of the exterior proximal section 136.

The sleeve 130 includes a hollow interior 142 which is defined by a series of internal surfaces including an internal proximally expanding conical section 144 distally extending from the proximal face 132 to an inner annular ring 146. An interior intermediate cylindrical section 148 extends distally from the annular ring 146 to an interior transition 150. An interior distally expanding conical section 152 extends distally from the interior transition 150 to the distal face 134. The annular ring 146 includes a proximal surface 154, a cylindrical inner surface 156 and a distal surface 158. The proximal and distal surfaces 154, 158 extend radially inward from the adjacent internal surfaces of the wall structure of the sleeve 130. The conical arrangements of the sleeve 130 depicted in FIGS. 4A and 4B work together to facilitate the sleeve folding back on itself as the helical anchor 66 screws increasingly deeper into cardiac tissue abutting against the distal face 134 of the sleeve 130.

While the embodiment depicted in FIGS. 4A and 4B is described as having an exterior distal conical section 140 and an interior distal conical section 152, in other embodiments, these two distal conical sections 140, 152 may be simply cylindrical such that the two distal sections 140, 152 simply extend from their immediately adjacent proximal sections, the sleeve thereby having and overall cylindrical inner and outer shape over its entirety distal the annular ring 146.

In one embodiment, the sleeve 130 is made of a low-durometer medical grade polymeric material such as a liquid silicone rubber (LSR) elastomer urethane, expanded polytetrafluoroethylene (EPTFE), or most any biocompatible soft thermoplastic, biocompatibie textile, or biocompatible woven composite, wherein any of the aforementioned materials form the sleeve 130 and a radiopaque additive such as platinum, platinum-iridium alloy, tantalum, tungsten, $TiO_2$, $BaSO_4$, or etc. is added throughout the sleeve. Alternatively, in one embodiment, the radiopaque additive could be restricted to a subsection of the sleeve such as the distal section 140 or extreme distal edge of the sleeve 130. In one embodiment, the sleeve may have a radiopaque marker in the form of a ring, beads or ring segments extending along a distal circumference or extreme distal circumferential edge of the sleeve 130. In such an embodiment, the radiopaque ring, beads or ring segments may be inserts molded into the sleeve, the inserts being in the form of a radiopaque material such as platinum, platinum-iridium alloy, tantalum, tungsten, $TiO_2$, $BaSO_4$, or etc.

Figure 5:
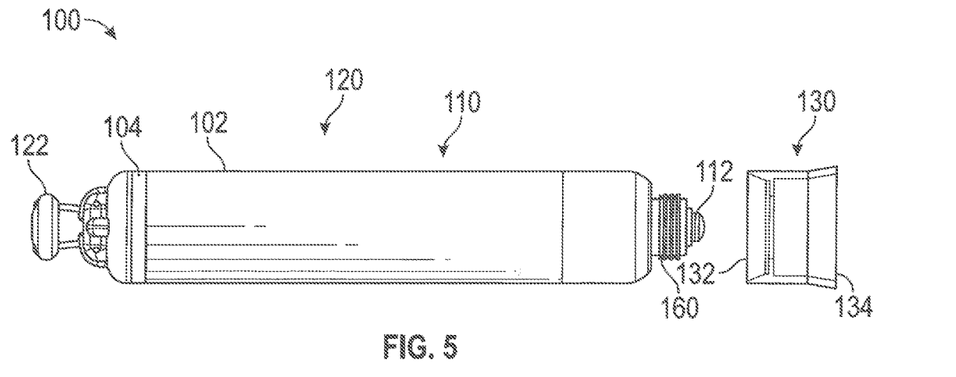
FIGS. 5 and 6 are both the same view of the leadless pulse generator depicted in FIG. 3, except showing the progressive assembly of the sleeve onto the distal end of the leadless pulse generator.
Figure 6:
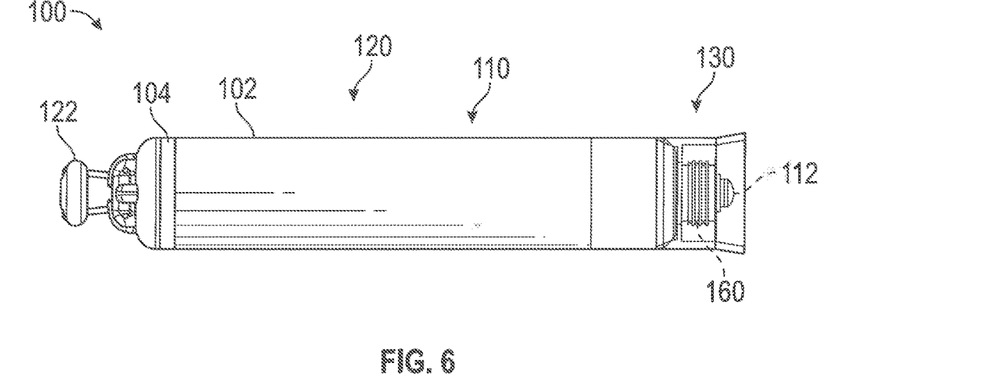

To discuss the assembly of the sleeve 130 onto the distal end of the leadless pulse generator 120, reference is made to FIGS. 5 and 6, which are both the same view of the leadless pulse generator 120 depicted in FIG. 3, except showing the progressive assembly of the sleeve onto the distal end of the leadless pulse generator. As shown in FIG. 5, the anchor mount 131 and helical anchor 66 are absent from the distal end of the leadless pulse generator 120, revealing a threaded distal protrusion 160 of the housing 102, the protrusion 160 extending circumferentially about the distal electrode 112. To begin the assembly, the sleeve 130 is coaxially aligned with the longitudinal axis of the leadless pulse generator with the proximal face 132 of the sheath 130 facing the distal end of the leadless pulse generator 130 and the distal face 134 of the sheath 130 facing away from the leadless pulse generator.

As shown in FIG. 6 and with reference to FIGS. 4A, 4B and 5, the sleeve 130 is then seated against the distal end of the leadless pulse generator 120 such that the threaded distal protrusion 160 and electrode 112 extend through the hollow interior 142 of the sleeve 130, the proximal conical surface 144 of the sleeve matingly abutting against a complementary conical surface of the distal end of the housing 102, the proximal surface 154 of the inner annular ring 148 of the sleeve abutting against a distal face of the distal end of the housing 102, and the cylindrical inner surface 156 of the annular ring 146 of the sleeve 130 making circumferential surface contact with an outer cylindrical surface of the threaded distal protrusion 160 of the housing 102.

As depicted in FIG. 3 and with reference to FIGS. 4A-6, the sleeve 130 is then secured in place by the anchor mount 131 being threaded or otherwise secured on the distal protrusion 160 of the housing 102 such that the inner annular ring 146 is sandwiched between a proximal end of the anchor mount and the distal end of the housing 102.

In some embodiments, the compressible radiopaque (or at least partially radiopaque) fixation sleeve 130 will have configurations different than that depicted in FIGS. 3-6, but will still employ an inner annular ring 146 that is sandwiched between the anchor mount 131 and the housing 102 for securing the sleeve 130 to the housing 102. For example and as discussed in detail below, the sleeve 130 may have a bellows configuration (see FIGS. 7A-7D), a tubular configuration (see FIGS. 8A and 8B), a slit tubular configuration (see FIGS. 9A and 9B), and a tine configuration (see FIGS. 10A and 10B). Each of the configurations will now be discussed in turn.

Figure 7A:
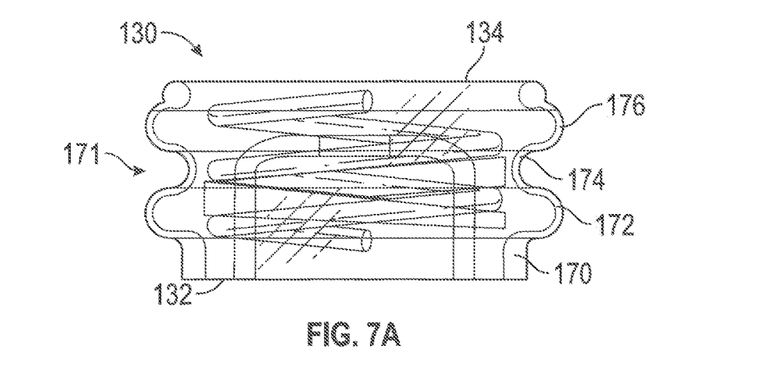
FIGS. 7A and 7B are, respectively, a side elevation and a cross-sectional elevation of a bellows radiopaque (or at least partially radiopaque) compressible fixation sleeve in a non-compressed state about an anchor mount and its anchor.
Figure 7B:
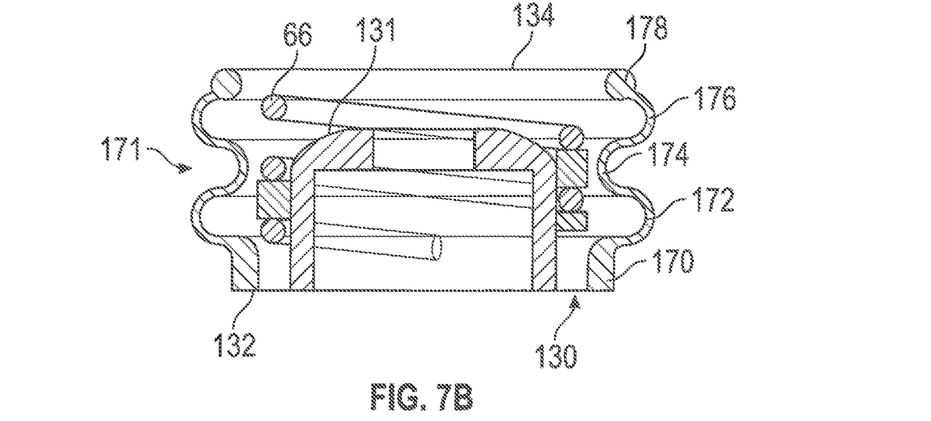
Figure 7C:
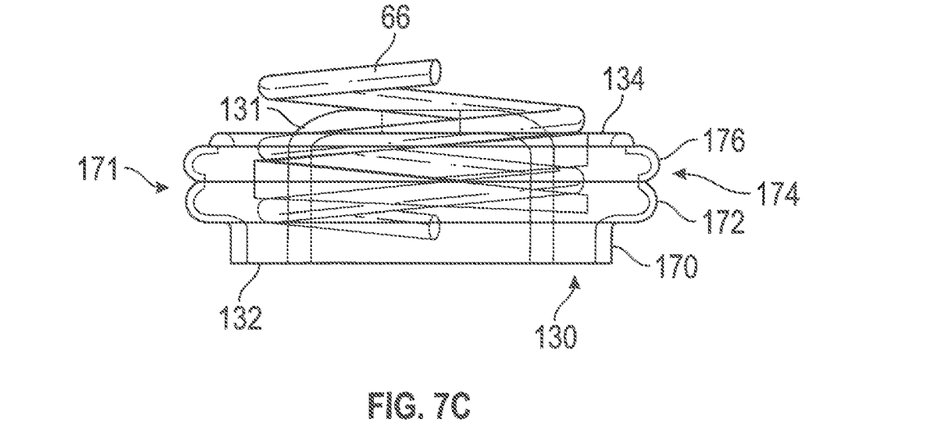
FIGS. 7C and 7D are, respectively, a side elevation and a cross-sectional elevation of the bellows radiopaque (or at least partially radiopaque) compressible fixation sleeve in a compressed state about the anchor mount and its anchor.
Figure 7D:
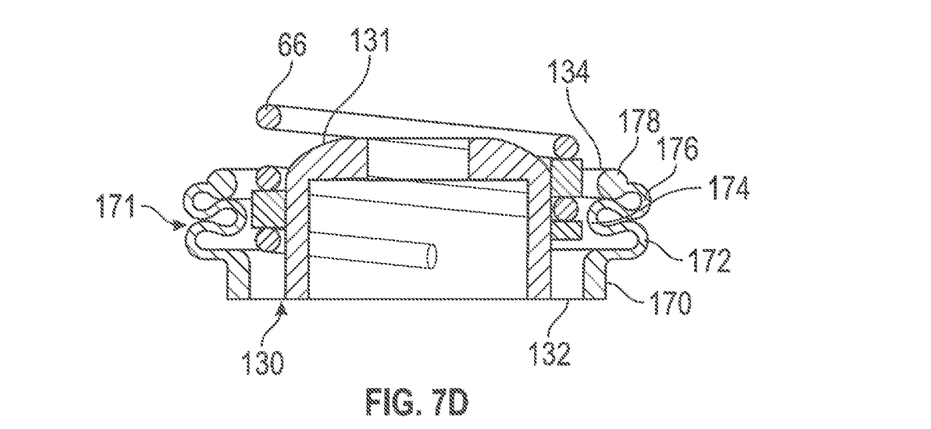

FIGS. 7A-7D illustrate the bellows sleeve 130, wherein FIGS. 7A and 7B are, respectively, a side elevation and a cross-sectional elevation of the bellows radiopaque (or at least partially radiopaque) compressible fixation sleeve in a non-compressed state (i.e., its biased state) about an anchor mount 131 and its anchor 66, and FIGS. 7C and 7D are, respectively, the same views, except showing the bellows sleeve 130 in a compressed state about the anchor mount 131 and its anchor 66. As can be understood from FIGS. 7A and 7B, the sidewall of the bellows sleeve 130 extends in a serpentine fashion between the proximal face 132 and the distal face 134 of the sleeve 130. The wall structure of the sleeve 130 includes a cylindrical section 170 extending distally from the proximal face 132 to the proximal boundary of a bellows structure 171 of the sleeve 130. Although not illustrated in FIGS. 7A-7D, in one embodiment, the inner annular ring 146 discussed above with respect to FIGS. 4A and 4B may be similarly locate in the cylindrical section 170 of the bellows sleeve 130 depicted in FIGS. 7A-7D for purposes of securing the bellows sleeve 130 to the housing 102 of the leadless pulse generator in a manner as discussed with respect to FIGS. 3-6 above.

Referring to FIGS. 7A and 7B and continuing proximal to distal along the bellows structure 171 from the cylindrical section 170, the bellows structure 171 proximally begins with a first arcuate radially outward projecting and circumferentially extending ridge 172. The first ridge 172 transitions into an arcuate radially inward projecting and circumferentially extending valley 174. The valley 174 transitions into a second arcuate radially outward projecting and circumferentially extending ridge 176 that transitions into a distal ringed terminus 178 of the sleeve 130, the distal edge of the distal ringed terminus 178 of the sleeve 130 forming the distal face 134 of the sleeve 130. The distal ringed terminus 178 may have a circular cross-section, In one embodiment, the distal ringed terminus 178 may be made of a radiopaque pliable polymer material or be a radiopaque ring imbedded in the pliable polymer material forming the rest of the sleeve 130

When the bellows sleeve 130 is compressed from the non-compressed state of FIGS. 7A and 7B to the compressed state of FIGS. 7C and 7D, the bellows structure 171 compresses proximal-distal, its first and second ridges 172, 176 abutting together on account of the valley 174 having collapsed radially inward and proximal-distal. Thus, while the helical anchor 66 is hidden within the circumferential confines of the bellows sleeve 130 when the sleeve 130 is in the non-compressed state depicted in FIGS. 7A and 7B, a distal region of the helical anchor 66 is exposed when the sleeve 130 is in the compressed state depicted in FIGS. 7C and 7D on account of the distal face 134 having been compressed proximally closer to the proximal face 132.

Figure 8A:
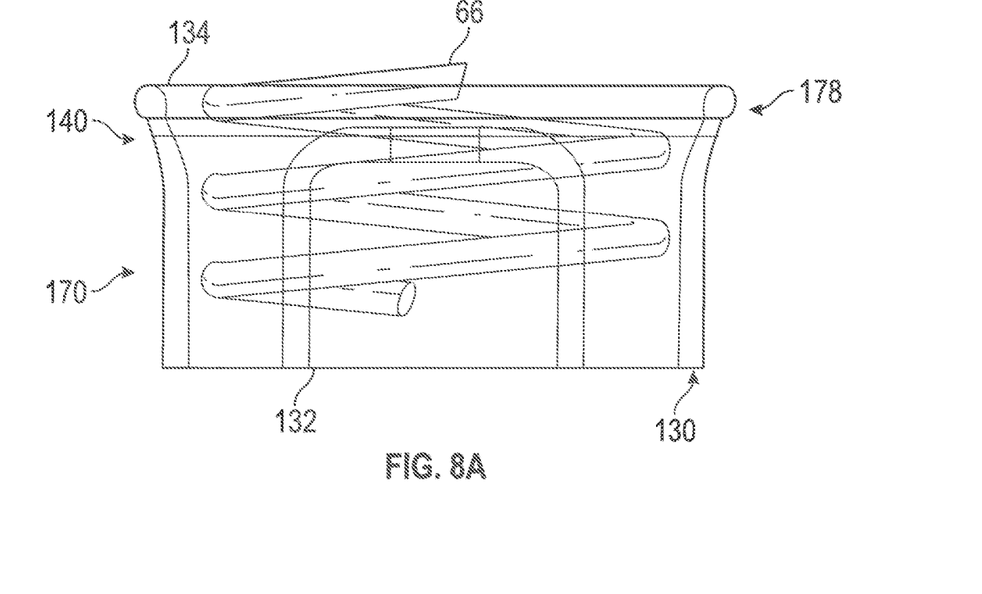
FIG. 8A is a side elevation of a tubular radiopaque (or at least partially radiopaque) compressible fixation sleeve in a non-compressed state about an anchor mount and its anchor.
Figure 8B:
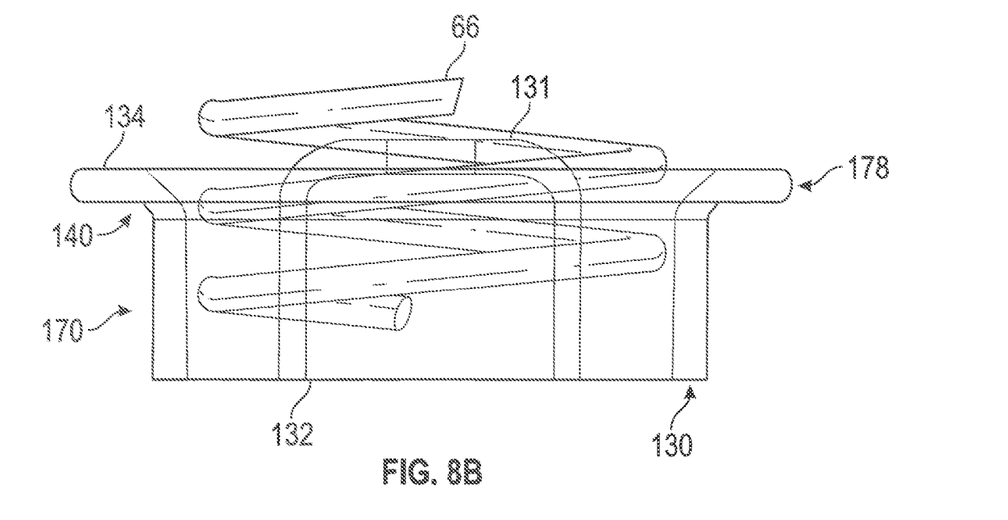
FIG. 8B is the same view as FIG. 8A, except showing the tubular sleeve in a compressed state about the anchor mount and its anchor.

FIGS. 8A and 8B illustrate the tubular sleeve 130, wherein FIG. 8A is a side elevation of a tubular radiopaque (or at least partially radiopaque) compressible fixation sleeve in a non-compressed state (i.e., its biased state) about an anchor mount 131 and its anchor 66, and FIG. 8B is the same view, except showing the tubular sleeve 130 in a compressed state about the anchor mount 131 and its anchor 66. As can be understood from FIG. 8A, the sidewall of the tubular sleeve 130 extends in a generally tubular or cylindrical fashion moving distally from the proximal face 132 until the wall structure of the sleeve radially flairs outward in a generally conical fashion a distal third of the sleeve 130 distally ending at the distal face 134 of the sleeve 130. Thus, the wall structure of the sleeve 130 includes a proximal cylindrical section 170 extending distally from the proximal face 132 to the proximal boundary of a distal conical section 140 of the sleeve 130. The distal conical section 140 distally transitions into a distal ringed terminus 178 of the sleeve 130. The distal edge of the distal ringed terminus 178 of the sleeve 130 forms the distal face 134 of the sleeve 130. The distal ringed terminus 178 may have a circular cross-section.

Although not illustrated in FIGS. 8A and 8B, in one embodiment, the inner annular ring 146 discussed above with respect to FIGS. 4A and 4B may be similarly locate in the cylindrical section 170 of the tubular sleeve 130 depicted in FIGS. 8A and 8B for purposes of securing the tubular sleeve 130 to the housing 102 of the leadless pulse generator in a manner as discussed with respect to FIGS. 3-6 above.

When the tubular sleeve 130 is compressed from the non-compressed state of FIG. 8A to the compressed state of FIG. 8B, the distal conical section 140 proximally folds back on itself and radially outwardly expands in diameter. Thus, while the helical anchor 66 is hidden within the circumferential confines of the tubular sleeve 130 when the sleeve 130 is in the non-compressed state depicted in FIG. 8A, a distal region of the helical anchor 66 is exposed when the sleeve 130 is in the compressed state depicted in FIG. 8B on account of the distal face 134 having been compressed proximally closer to the proximal face 132.

As can be understood from a comparison of FIGS. 8A and 8B, the sleeve 130 is configured such that, in the course of the helical anchor 66 screwing into the cardiac tissue and the distal face 134 being forced against the cardiac tissue, thereby transitioning the sleeve 130 from its biased state (FIG. 8A) to its deflected state (FIG. 8B), the distal section 140 folds proximally and the distal face 134 increases in diameter. Also, the distal face 134 changes from facing distally to facing radially outward when the distal face 134 displaces proximally towards the proximal face 132.

Figure 9A:
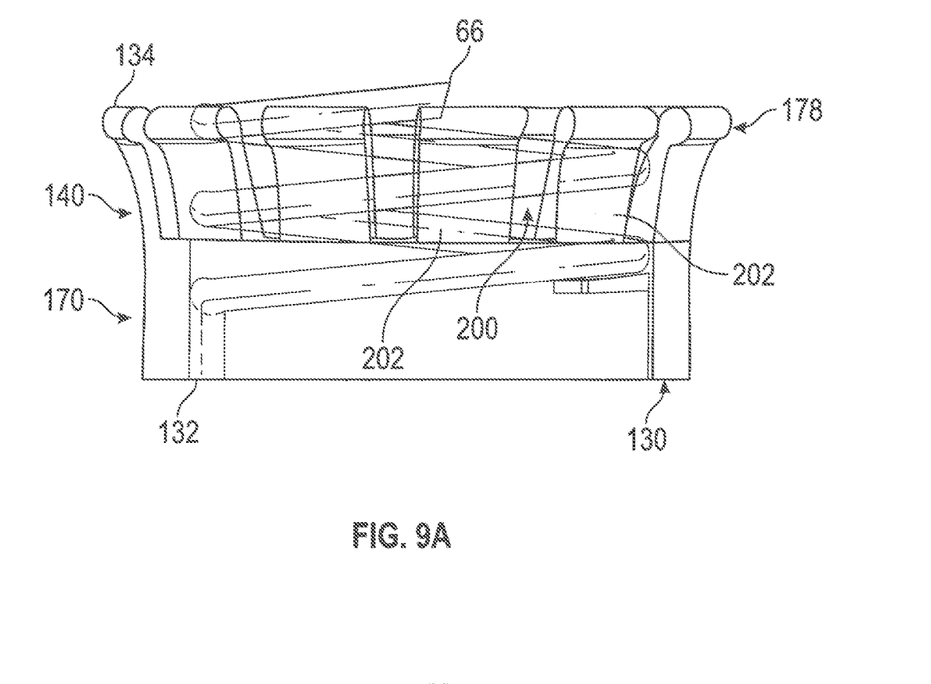
FIG. 9A is a side elevation of a slit tubular radiopaque (or at least partially radiopaque) compressible fixation sleeve in a non-compressed state about an anchor mount and its anchor.
Figure 9B:
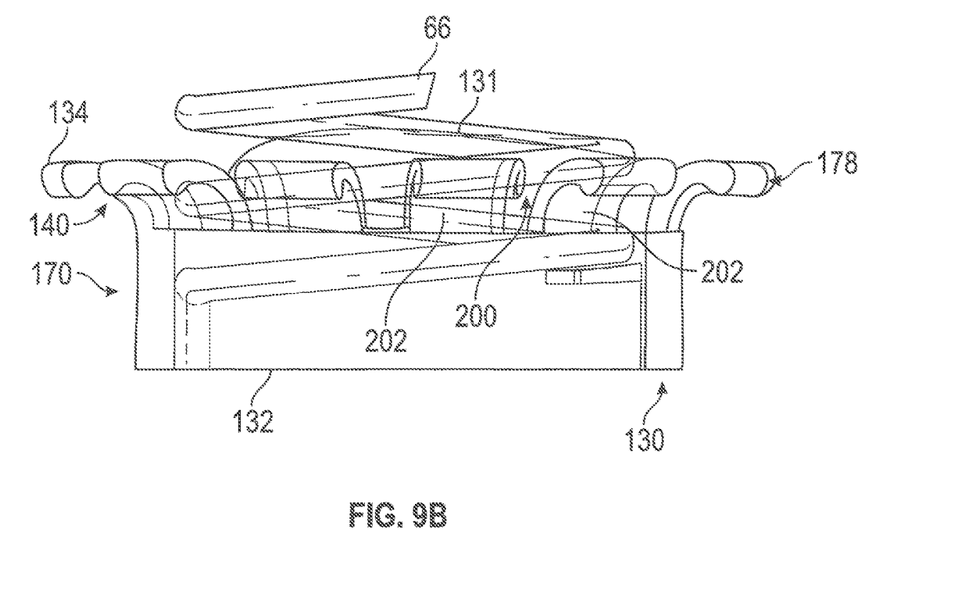
FIG. 9B is the same view as FIG. 9A, except showing the slit tubular sleeve in a compressed state about the anchor mount and its anchor.

FIGS. 9A and 9B illustrate the slit tubular sleeve 130, wherein FIG. 9A is a side elevation of a slit tubular radiopaque (or at least partially radiopaque) compressible fixation sleeve in a non-compressed state (i.e., its biased state) about an anchor mount 131 and its anchor 66, and FIG. 9B is the same view, except showing the slit tubular sleeve 130 in a compressed state about the anchor mount 131 and its anchor 66.

As can be understood from a comparison of the tubular embodiment depicted in FIGS. 8A and 8B to the slit tubular embodiment of FIGS. 9A and 9B, the two embodiments are substantially similar, except the distal conical region 140 of the slit tubular embodiment of FIGS. 9A and 9B includes a series of relatively narrow gaps 200 defined in the distal conical section 140 of the slit tubular embodiment of FIGS. 9A and 9B. Specifically, the distal conical section 140 of the slit tubular embodiment of FIGS. 9A and 9B includes a series of longitudinally extending slits or slots 200 extending the length of the distal conical section 140, and these slits 200 are evenly distributed about the circumference of the distal conical section 140. The slits 200 may be rectangular shaped or any other shape. The slits 200 define a series of longitudinally extending readily pliable members 202 that are evenly distributed about the circumference of the distal conical section 140. The members 202 may be rectangular shaped or any other shape.

Although not illustrated in FIGS. 9A and 9B, in one embodiment, the inner annular ring 146 discussed above with respect to FIGS. 4A and 4B may be similarly locate in the cylindrical section 170 of the slit tubular sleeve 130 depicted in FIGS. 9A and 9B for purposes of securing the slit tubular sleeve 130 to the housing 102 of the leadless pulse generator in a manner as discussed with respect to FIGS. 3-6 above.

When the slit tubular sleeve 130 is compressed from the non-compressed state of FIG. 9A to the compressed state of FIG. 9B, the members 202 of the distal conical section 140 proximally fold back on themselves and radially outwardly splay in an increased diameter. Thus, while the helical anchor 66 is hidden within the circumferential confines of the slit tubular sleeve 130 when the sleeve 130 is in the non-compressed state depicted in FIG. 9A, a distal region of the helical anchor 66 is exposed when the sleeve 130 is in the compressed state depicted in FIG. 9B on account of the distal face 134 having been compressed proximally closer to the proximal face 132.

As can be understood from a comparison of FIGS. 9A and 9B, the sleeve 130 is configured such that, in the course of the helical anchor 66 screwing into the cardiac tissue and the distal face 134 being forced against the cardiac tissue, thereby transitioning the sleeve 130 from its biased state (FIG. 9A) to its deflected state (FIG. 9B), the distal section 140 folds proximally and the distal face 134 increases in diameter. Also, the distal face 134 changes from facing distally to facing radially outward when the distal face 134 displaces proximally towards the proximal face 132, Further, the members 202 change from projecting distally to projecting radially outward when the distal face 134 displaces proximally towards the proximal face 132.

Figure 10A:
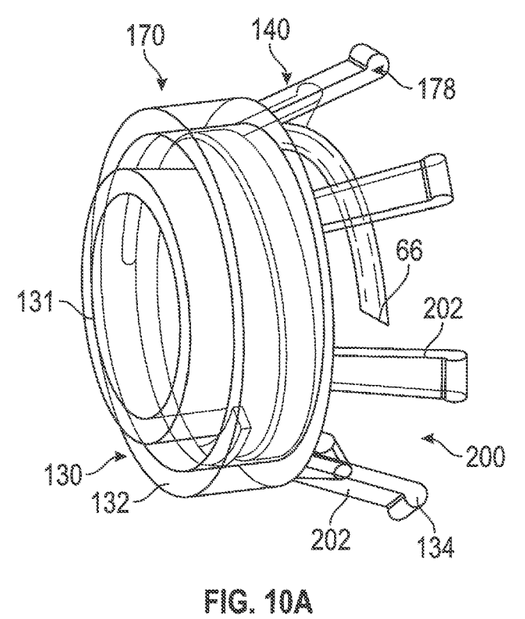
FIG. 10A is a side elevation of a tined tubular radiopaque (or at least partially radiopaque) compressible fixation sleeve in a non-compressed state about an anchor mount and its anchor.
Figure 10B:
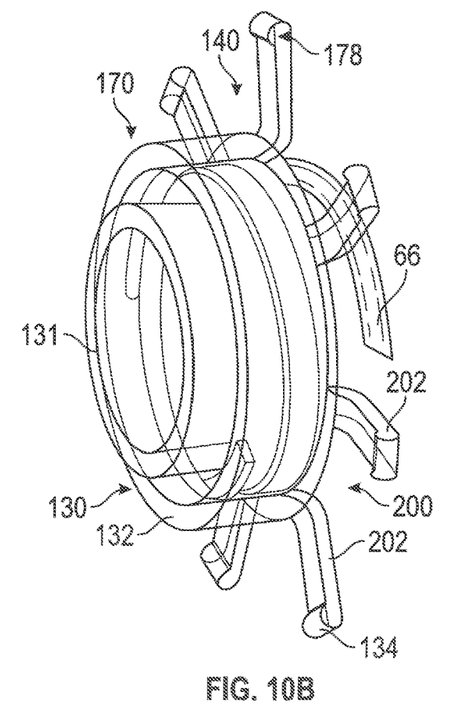
FIG. 10B is the same view as FIG. 10A, except showing the tined tubular sleeve in a compressed state about the anchor mount and its anchor.

As can be understood from a comparison of the slit tubular embodiment depicted in FIGS. 9A and 9B to the tined tubular embodiment of FIGS. 10A and 10B, the two embodiments are substantially similar, except the slit tubular embodiment of FIGS. 9A and 9B includes a series of relatively narrow gaps 200 and a series of relatively wide members 202 while the tined tubular embodiment includes a series of relatively wide gaps 200 and a series of relatively narrow pliable members 202 that may be considered pliable fines 202. Specifically, the distal conical section 140 of the tined tubular embodiment of FIGS. 10A and 10B includes a series of longitudinally extending slits or slots 200 extending the length of the distal conical section 140, and these slits 200 are evenly distributed about the circumference of the distal conical section 140. The slits 200 may be rectangular shaped or any other shape. The slits 200 define a series of longitudinally extending readily pliable members or tines 202 that are evenly distributed about the circumference of the distal conical section 140. The members 202 may be rectangular shaped or any other shape.

Although not illustrated in FIGS. 10A and 10B, in one embodiment, the inner annular ring 146 discussed above with respect to FIGS. 4A and 4B may be similarly locate in the cylindrical section 170 of the tined tubular sleeve 130 depicted in FIGS. 10A and 10B for purposes of securing the tined tubular sleeve 130 to the housing 102 of the leadless pulse generator in a manner as discussed with respect to FIGS. 3-6 above.

When the tined tubular sleeve 130 is compressed from the non-compressed state (i.e., its biased state) of FIG. 10A to the compressed state of FIG. 10B, the members or tines 202 of the distal conical section 140 proximally fold back on themselves and radially outwardly splay in an increased diameter. Thus, while the helical anchor 66 is hidden within the circumferential confines of the tined tubular sleeve 130 when the sleeve 130 is in the non-compressed state depicted in FIG. 10A, a distal region of the helical anchor 66 is exposed when the sleeve 130 is in the compressed state depicted in FIG. 10B on account of the distal face 134 having been compressed proximally closer to the proximal face 132.

As can be understood from a comparison of FIGS. 10A and 10B, the sleeve 130 is configured such that, in the course of the helical anchor 66 screwing into the cardiac tissue and the distal face 134 being forced against the cardiac tissue, thereby transitioning the sleeve 130 from its biased state (FIG. 10A) to its deflected state (FIG. 10B), the distal section 140 folds proximally and the distal face 134 increases in diameter. Also, the distal face 134 changes from facing distally to facing radially outward when the distal face 134 displaces proximally towards the proximal face 132. Further, the members 202 change from projecting distally to projecting radially outward when the distal face 134 displaces proximally towards the proximal face 132.

The following discussion pertains to a delivery method for implanting a leadless pulse generator 120 equipped with a fixation sleeve 130 such as any of those disclosed herein. The method begins with the leadless pulse generator 120 being tracked via delivery tools (e.g., a delivery catheter, etc.) through the patient vasculature to an implantation site in the patient's heart. Upon the distal end of the leadless pulse generator being placed against the implantation site, gentle forward pressure is applied on the delivery catheter until noticing a slight movement of the delivery catheter proximal to the leadless pulse generator and synchronous to the heartbeat. The curve of the catheter down to the inferior vena cave is visualized via fluoroscopy. The implant site and the distal region of the delivery tool(s), plus the leadless pulse generator 120 and its fixation sleeve 130, are visualized via fluoroscopy while the leadless pulse generator 120 is caused to rotate clockwise as the radiopaque marker 124 of the leadless pulse generator is observed, its turns being counted for the appropriate number of turns to cause the helical anchor 66 to screw fully into the cardiac tissue. Simultaneously, the distal face 134 of the radiopaque fixation sleeve 130 and the helical anchor 66 are observed via fluoroscopy, including the positional relationship of the distal face 134 of the sleeve 130 relative to the anchor 66.

While visualizing the radiopaque fixation sleeve during the rotation of the leadless pulse generator 120, if the distal tip electrode 112 remains proximal to the distal face 134 of the fixation sleeve 130, the implanter can safely continue rotating the leadless pulse generator until alignment is observed. Once the helical anchor 66 is adequately imbedded in the cardiac tissue, as can be understood from the relationship of the distal face 134 of the fixation sleeve 130 relative to the distal tip electrode 112 and/or the helical anchor 66, the implanter can uncouple the leadless pulse generator 120 from the delivery tool(s) with confidence that the leadless pulse generator 120 is securely anchored to the engaged cardiac tissue.

As noted above, the fixation sleeve equipped leadless pulse generator 120 disclosed herein is advantageous for a number of reasons. First, the protective sleeve 130 prevents helical anchor engagement or deformation due to inadvertent snagging of cardiac tissue. Second, the compressible sleeve 130 allows fluoroscopic evaluation of distance between cardiac tissue and the distal end electrode 112, thereby conveying information to the implanter regarding whether or not the anchor 66 is properly screwing into cardiac tissue and to what extent. Third, the compressible sleeve 130 provides resistance against over-rotation of the leadless pulse generator during implant. Fourth, the compressible sleeve 130 provides additional contact surface area to reduce contact pressure and mitigate tissue damage. Fifth, the compressible sleeve forms a seal against the endocardium to reduce the possibility of effusion through any potential microperforation created by the helical anchor 66 extending through the thin myocardium. Finally, the compressible sleeve 130 with tines or other radially splaying members 202 can act to prevent anti-rotation of an implanted leadless pulse generator 120.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of manufacturing a leadless pulse generator, the method comprising:

positioning a distal electrode of the leadless pulse generator within a hollow interior of a compressible fixation sleeve including at least a radiopaque portion; and coupling the compressible fixation sleeve to the housing of the leadless pulse generator by coupling an anchor mount to the housing such that a portion of the compressible fixation sleeve is sandwiched between the anchor mount and a portion of the housing.

2. The method of claim 1, wherein the portion of the compressible fixation sleeve comprises an inner annular ring.

3. The method of claim 1, wherein the housing comprises a distal protrusion that boarders the distal electrode and is also positioned in the hollow inferior.

4. The method of claim 3, wherein the distal protrusion mechanically couples with the anchor mount when the anchor mount is coupled to the housing.

5. The method of claim 4, wherein the distal protrusion and the anchor mount threadably engage with each other in the course of being mechanically coupled with each other.

* * * * *